(12) United States Patent
Kim

(10) Patent No.: US 10,507,010 B1
(45) Date of Patent: Dec. 17, 2019

(54) STOOL MONITORING AND HEALTH GUIDANCE APPARATUS

(71) Applicant: Hong Min Kim, Toronto (CA)

(72) Inventor: Hong Min Kim, Toronto (CA)

(*) Notice: Subject to any disclaimer, the term of this patent is extended or adjusted under 35 U.S.C. 154(b) by 0 days.

(21) Appl. No.: 16/350,039

(22) Filed: Sep. 18, 2018

(51) Int. Cl.
| | |
|---|---|
| *A61B 10/00* | (2006.01) |
| *G01N 21/31* | (2006.01) |
| *A61B 5/00* | (2006.01) |
| *G01N 21/84* | (2006.01) |
| *E03D 9/00* | (2006.01) |
| *G01N 33/483* | (2006.01) |

(52) U.S. Cl.
CPC ........ *A61B 10/0038* (2013.01); *A61B 5/0002* (2013.01); *G01N 21/314* (2013.01); *G01N 21/84* (2013.01); *E03D 9/00* (2013.01); *G01N 33/4833* (2013.01)

(58) Field of Classification Search
CPC .................................................. A61B 10/0038
USPC ............................................................. 4/661
See application file for complete search history.

(56) References Cited

U.S. PATENT DOCUMENTS

| | | | | | |
|---|---|---|---|---|---|
| 5,196,167 | A | * | 3/1993 | Guadagno | G01N 33/726 422/421 |
| 5,217,874 | A | * | 6/1993 | Guadagno | G01N 33/726 422/421 |
| 5,698,095 | A | * | 12/1997 | Kami | C02F 1/048 210/173 |
| 5,741,650 | A | * | 4/1998 | Lapidus | C12Q 1/6806 435/6.11 |
| 5,952,178 | A | * | 9/1999 | Lapidus | C12Q 1/6806 435/6.11 |
| 7,194,776 | B1 | * | 3/2007 | Lastuka | E03D 13/00 340/603 |
| 7,195,878 | B2 | * | 3/2007 | Cleator | B01L 3/505 435/283.1 |
| 7,833,794 | B2 | * | 11/2010 | LaStella | A61B 10/0038 422/404 |
| 8,304,596 | B2 | * | 11/2012 | LaStella | A61B 10/0038 422/409 |
| 8,679,420 | B2 | * | 3/2014 | LaStella | A61B 10/0038 422/401 |
| 8,802,442 | B2 | * | 8/2014 | Wheeldon | G01N 21/75 250/459.1 |

* cited by examiner

*Primary Examiner* — Lori L Baker

(74) *Attorney, Agent, or Firm* — David W Wong

(57) ABSTRACT

A stool monitoring and health guidance system is provide with a color sensor and an image sensor mountable at the toilet seat of a toilet to detect the color and physical properties of stools deposited in the toilet in bowel movement. The system provides a sanitary and convenient means to examine the stool without having to obtain a specimen from the stool directly, and providing guidance to the user of possible health issues.

10 Claims, 2 Drawing Sheets

STOOL MONITORING AND HEALTH GUIDANCE APPARATUS

BACKGROUND OF THE INVENTION

This invention relates to an apparatus for monitoring the condition and properties of stools excreted in bowel movement by a person for providing guidance of health condition of the person. It also provides guidance to the user in maintaining a healthy diet and digestive system.

BACKGROUND ART

Stool properties or conditions such as stool consistency, color, shape and regularity can provide distinctive indications of a person's health condition and/or possible health concerns. The stool of a healthy person consists of 75 percent water and 25 percent bacteria and fiber. It normally has a rich brown color, a putty consistency, and a sausage-like shape. Stool may have different colors for various reasons, and depending highly on a person's diet, which may not be of any health concern. Occasional changes in color may not require emergency attention; but recurrence of changes in color and/or consistency would require further health examination, and occurrence of black, red, or maroon stools can be due to bleeding and are possibility of health concerns that would alert the user to seek urgent medical assessment and treatment.

Following is a chart outlining various stool colors that require further medical attentions.

| STOOL COLOR | HEALTH CONCERN | HEALTH ATTENTION |
| --- | --- | --- |
| Black | May just due to rich in iron and bismuth but can indicate gastro-bleeding | Requires emergency medical attention |
| Maroon | Gastro-bleeding | Requires emergency medical attention |
| Red | Hemorrhoid, inflammatory bowel disease, infection, diverticular bleeding, tumor, rapid upper gastro-bleeding | Requires emergency medical attention |
| Green | May be normal, or due to high in vegetable diet | Consult health care professional |
| Green associated with diarrhea | Stomach bacterial infection | Requires medical attention |
| Brown | Normal | |
| Yellow | Mal-absorption due to diseases of the pancreas; celiac disease; cystic fibrosis; or giardia infection | Requires medical attention |
| Clay, pale yellow or white | Lack of bile in the stool due to liver or biliary disease | Requires medical attention |

Changes in stool condition are often not a concern. However, a person experiences sudden new stool physical changes such as in diameter, length, and size in the bowel movement, should consult a health care professional for further investigation as it may be a sign of a narrowed or scarred colon, or perhaps due to a tumor. The health care professional would conduct further tests and would review further information about accompanying symptoms to determine any possible health issues.

Stools that are hard and in the form of small pellets indicate generally insufficient fiber in the body system to flush the body waste out of the digestive system, and the stool is staying in the body longer than it should such that the colon keeps extracting water out of it, which results in turning it into hard pieces. The solution is usually simple by drinking sufficient amount of water.

Heretofore in order to examine stool condition to determine any required health issue, it has been necessary to obtain a specimen of the stool either directly from the stool or from an article such as a diaper worn by the person. Such procedure is rather messy and unpleasant and often difficult to carry out. It also invariably exposes the person to fecal bacterial contamination in the handling and collecting of the stool specimen.

SUMMARY OF THE INVENTION

The principal object of the present invention is to provide an apparatus which can examine a person's stool conveniently without requiring handling of the stool.

Another object of the present invention is to provide an apparatus which can determine if medical attention is required depending on the color and shape of the stool.

Another object of the present invention is to provide an apparatus which conveniently monitors the stool condition deposited into a toilet to inform the user whether there are health concerns that require further medical attention.

It is another object of the present invention to provide an apparatus which is easy to operate.

It is yet another object of the present invention to provide an apparatus which can be easily incorporated in a toilet.

It is still another object of the present invention to provide an apparatus which provides a visual display of the results of examination of the stool and to provide alert of further medical attention required based on the results.

The stool monitoring and health guidance apparatus of the present invention comprises a color sensor mountable at the underside of a toilet seat mounted on a toilet, an image sensor also mountable at the underside of the toilet seat, a controller processor is connected to the color sensor and the image sensor. The controller processor is operative to receive a color signal from the color sensor detecting the color of stools deposited in the toilet bowl of the toilet, and to receive an image signal from the image sensor detecting the physical condition and properties of the stools. The controller processor correlates the color signal and the image signal to provide an analysis of possible health concerns and guidance of a person using the toilet for bowel movement. A visual display connected to the controller processor to receive and to display the results of the analysis of possible health guidance.

BRIEF DESCRIPTION OF THE DRAWINGS

Other objects and advantages of the present invention will become apparent from the following detailed description of the preferred embodiments thereof in connection with the accompanying drawings in which.

DETAILED DESCRIPTION OF THE PREFERRED EMBODIMENTS

Figure 1:
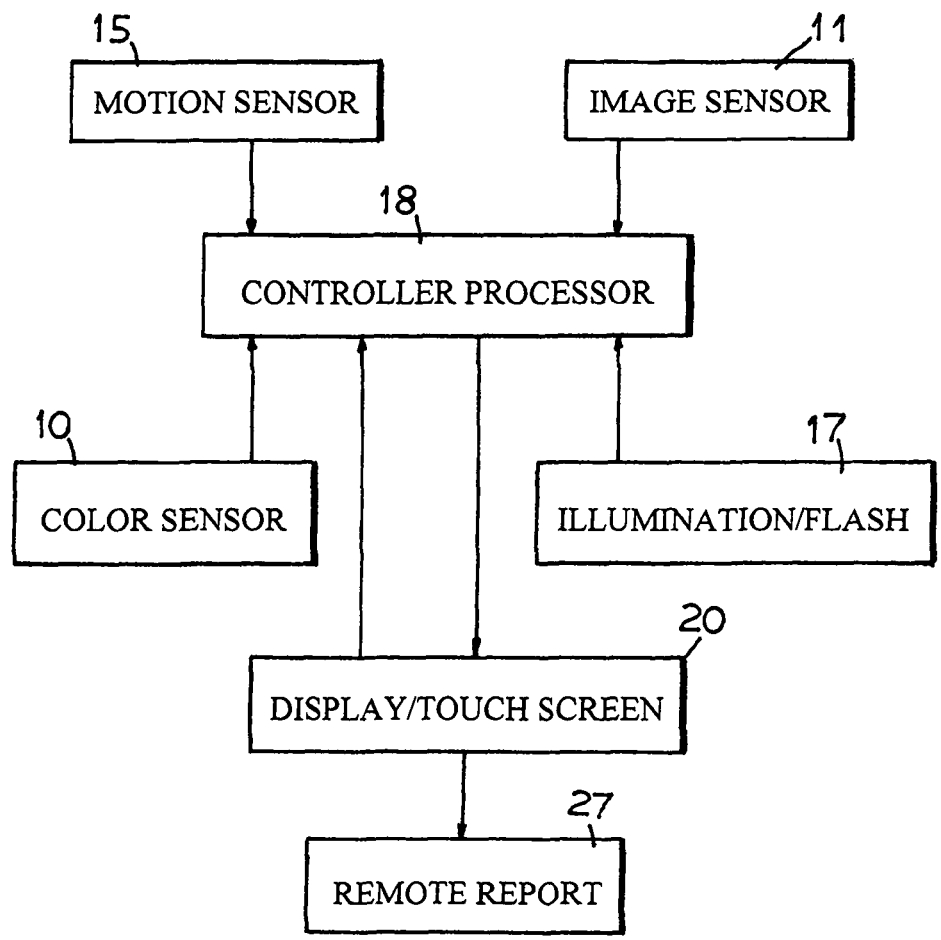
FIG. 1 is a schematic block diagram showing the construction of the apparatus according to the present invention.
Figure 2:
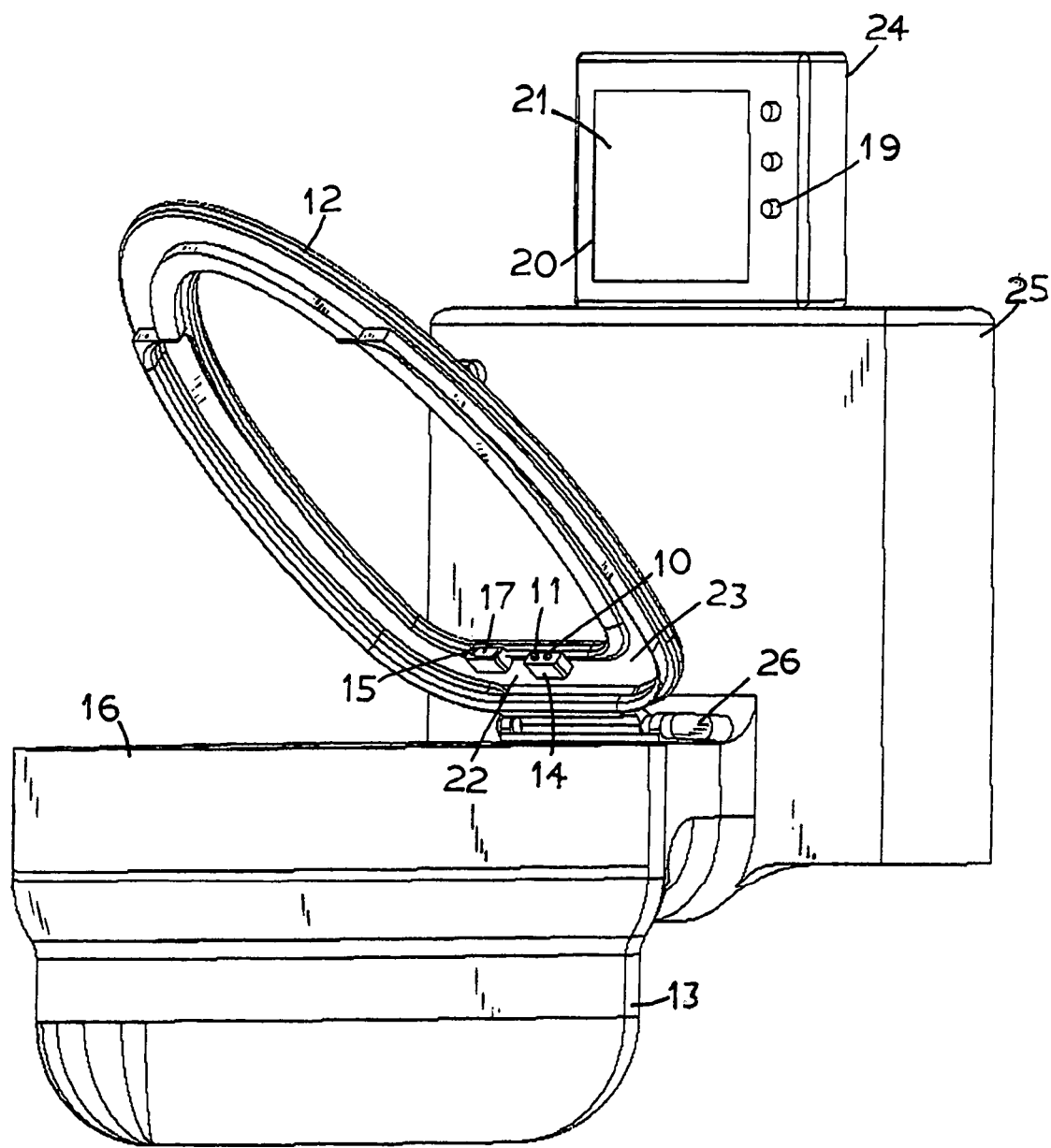
FIG. 2 is a perspective upper right side front view of a toilet having the apparatus of the present invention incorporated therein.

With reference to the accompanying drawings in which like reference numerals designates same component parts in the various views, the stool monitoring and health guidance apparatus of the present invention comprises of a color sensor 10 and an image sensor 11, mountable at the underside of a toilet seat 12 of a toilet such as a flush toilet 13. The two sensors may be provided in an integral single unit 14 as shown in the exemplary embodiment in FIG. 2. A motion sensor 15 is located under the toilet seat 12 for activating the apparatus when a person is sitting on the toilet for bowel movement. The color sensor 10 and the image sensor 11 detect the physical condition and properties including color and shape of the stool, and any trace of blood in the stool, deposited into the toilet bowl 16. An illumination lighting device 17 such as an LED light or a flash light can also be provided at the underside of the toilet seat 12 to enhance the lighting for the detection of the stools by the color sensor 10 and the image sensor 11. The lighting device 17 may be incorporated in the same integral physical unit as the motion sensor 15 to simplify the construction as shown in the exemplary embodiment in FIG. 2. The color sensor 10 and image sensor 11, and the lighting device 17 are orientated to aim at a predetermined location inside the toilet bowl in which the stool is deposited. A controller processor 18 receives the color signal from the color sensor 10 indicative of the color of the stools, and the controller processor 18 also receives the image signal from the image sensor 11 indicative of the physical shape and condition of the stool, for example, either diarrhea or firm. The controller processor 18 correlates the scanned color information and the image information of the physical condition and properties of the stool with a color histogram and stool physical condition and properties and health guidance according to the various combinations of normal and abnormal stool colors and physical conditions stored in a memory bank, and conducts an analysis of the information from the sensors to indicate whether there are possible health concerns. The result of the analysis by the controller processor 18 can be accessed by operating a key board or operating switches 19 connected to or provided at a display unit 20. The operating key board or operating switches 19 and display 20 may be provided as a single unit as shown in the exemplary embodiment in FIG. 2 in which the display is provided with a touch screen 21 which can serve also as an alternative operating panel.

As shown in the exemplary embodiment of the present invention, the integral sensor unit containing the color sensor 10 and image sensor 11, as well as the integral unit containing the motion sensor 15 and the lighting device 17 are mounted at the rear edge portion 22 of the undersurface 23 of the toilet seat 12. An enclosure casing 24 housing the controller processor 19 and the operating touch panel and display 20 can be conveniently located on top of the water reservoir 25 of the toilet. Alternatively, the enclosure casing 24 may be located adjacent to the toilet 13 to facilitate its operation by the user.

The wiring connecting the color sensor 10, the image sensor 11, the motion sensor 15, and the lighting device 17, to the controller processor 18 located in the enclosure casing 24 is routed through a conduit 26 located at the hinge mounting of the toilet seat 12 to the toilet bowl 16.

A printer 27 may be connected to the controller processor 18 such that a printed copy of the results of the monitoring operation may be obtained.

What is claimed is:

1. A stool monitoring and health guidance apparatus comprising:

a color sensor mounted at an underside of a toilet seat for a toilet;

an image sensor also mounted at said underside of said toilet seat;

a controller processor connected to said color sensor and said image sensor, said controller processor being operative for receiving a color signal from said color sensor detecting color of stools deposited in a toilet bowl of said toilet, and also receiving an image signal from said image sensor detecting physical condition and property of said stools, said controller processor including a memory bank containing a color histogram of stool colors and physical conditions, and health concerns and guidance with respect to various combinations of stool colors and physical conditions, and said controller processor correlating said color signal and said image signal for generating an analysis of possible health concerns and guidance for a person using said toilet for bowel movement;

a visual display unit connected to said controller processor and operative for receiving results of said analysis from said controller processor for displaying said guidance.

2. A stool monitoring and health guidance apparatus according to claim 1 including an illumination lighting device mounted at said underside of said toilet seat, said lighting device being operative for illuminating stools deposited in said toilet for enhancing detection of color and physical condition and properties by said color sensor and said image sensor of said stools deposited in said toilet.

3. A stool monitoring and health guidance apparatus according to claim 2 including a motion sensor mounted on said toilet seat and operative for activating said apparatus when the person sits on said toilet for bowel movement.

4. A stool monitoring and health guidance apparatus according to claim 3 including operating switches provided at said visual display unit and connected to said controller processor, said switches being operative for requesting said controller processor for sending and displaying said results of health concerns and guidance on said visual display unit.

5. A stool monitoring and health guidance apparatus according claim 4 wherein said image sensor, said color sensor, and said lighting device are oriented to aim at stools deposited at a predetermined location inside said toilet bowl.

6. A stool monitoring and health guidance apparatus according to claim 5 wherein said color sensor and said image sensor are provided in a single integral unit.

7. A stool monitoring and health guidance apparatus according to claim 6 wherein said lighting device and said motion sensor are provided in a second integral unit.

8. A stool monitoring and health guidance apparatus according to claim 7 wherein said controller processor and visual display are enclosed in a housing located on top of a water tank of said toilet.

9. A stool monitoring and health guidance apparatus according to claim 8 wherein said lighting device is an LED light.

10. A stool monitoring and health guidance apparatus according to claim 8 wherein said lighting device is a flash light.

* * * * *